(12) United States Patent
El-Baz et al.

(10) Patent No.: US 11,875,892 B2
(45) Date of Patent: Jan. 16, 2024

(54) SEGMENTATION OF MEDICAL IMAGES

(71) Applicants: UNIVERSITY OF LOUISVILLE RESEARCH FOUNDATION, INC., Louisville, KY (US); SCIENCE AND TECHNOLOGY DEVELOPMENT FUND, Cairo (EG)

(72) Inventors: Ayman S. El-Baz, Louisville, KY (US); Ahmed Soliman, Louisville, KY (US); Moumen El-Melegy, Assuit (EG); Mohamed Abou El-Ghar, El Mansoura (EG)

(73) Assignee: University of Louisville Research Foundation, Inc., Louisville, KY (US)

( * ) Notice: Subject to any disclaimer, the term of this patent is extended or adjusted under 35 U.S.C. 154(b) by 222 days.

(21) Appl. No.: 16/628,795

(22) PCT Filed: Jul. 7, 2018

(86) PCT No.: PCT/US2018/041168
§ 371 (c)(1),
(2) Date: Jan. 6, 2020

(87) PCT Pub. No.: WO2019/010470
PCT Pub. Date: Jan. 10, 2019

(65) Prior Publication Data
US 2020/0203001 A1 Jun. 25, 2020

Related U.S. Application Data

(60) Provisional application No. 62/529,788, filed on Jul. 7, 2017.

(51) Int. Cl.
*G16H 30/40* (2018.01)
*G06T 7/11* (2017.01)
(Continued)

(52) U.S. Cl.
CPC ............... *G16H 30/40* (2018.01); *G06N 3/08* (2013.01); *G06N 7/01* (2023.01); *G06N 20/20* (2019.01);
(Continued)

(58) Field of Classification Search
CPC . G06T 2207/20081; G06T 2207/30016; G06T 7/0012
(Continued)

(56) References Cited

U.S. PATENT DOCUMENTS

2015/0286786 A1* 10/2015 El-Baz ...................... G06T 7/33
382/131
2017/0083793 A1* 3/2017 Shie ........................ G06V 10/82
2018/0070905 A1* 3/2018 El-Baz .................... G06T 7/149

OTHER PUBLICATIONS

Khadidos, A., et al.: Weighted level set evolution based on local edge features for medical image segmentation. IEEE Transactions on Image Processing (2017).
(Continued)

*Primary Examiner* — Ajibola A Akinyemi
(74) *Attorney, Agent, or Firm* — Dentons Bingham Greenebaum LLP; Brian W. Chellgren

(57) ABSTRACT

Methods for segmenting medical images from different modalities include integrating a plurality of types of quantitative image descriptors with a deep 3D convolutional neural network. The descriptors include: (i) a Gibbs energy for a prelearned 7th-order Markov-Gibbs random field (MGRF) model of visual appearance, (ii) an adaptive shape prior model, and (iii) a first-order appearance model of the original volume to be segmented. The neural network fuses the computed descriptors to obtain the final voxel-wise probabilities of the goal regions.

17 Claims, 1 Drawing Sheet

(51) Int. Cl.
  *G06N 20/20* (2019.01)
  *G06N 3/08* (2023.01)
  *G06N 7/01* (2023.01)

(52) U.S. Cl.
  CPC ...... *G06T 7/11* (2017.01); *G06T 2207/20081* (2013.01); *G06T 2207/20084* (2013.01)

(58) Field of Classification Search
  USPC .......................................................... 382/173
  See application file for complete search history.

(56) References Cited

OTHER PUBLICATIONS

Torbati, N., et al.: An efficient neural network based method for medical image segmentation. Computers in biology and medicine 44 (2014) 76-87.

Shen, T., et al.: Active volume models for medical image segmentation. IEEE transactions on medical imaging 30(3) (2011) 774-791.

Li, C., et al.: Supervised variational model with statistical inference and its application in medical image segmentation. IEEE Transactions on Biomedical Engineering 62(1) (2015) 196-207.

Glocker, B., et al.: Deformable medical image registration: Setting the state of the art with discrete methods. Annual Review of Biomedical Engineering 13 (2011) 219-244.

Lu, Y., et al.: Feature selection using principal feature analysis. In: Proceedings of the 15th ACM international conference on Multimedia, ACM (2007) 301-304.

El-Baz, A., et al.: Stochastic modeling for medical image analysis. CRC Press (2015).

Kamnitsas, K., et al.: Efficient multi-scale 3D CNN with fully connected CRF for accurate brain lesion segmentation. Medical Image Analysis 36 (2017) 61-78.

Gerig, G., et al.: Valmet: A new validation tool for assessing and improving 3D object segmentation. In: International Conference on Medical Image Computing and Computer-Assisted Intervention, Springer (2001) 516-523.

International Search Report and Written Opinion, dated Oct. 18, 2018—International application No. PCT/US2018/041168 Applicant: University of Louisville Research Foundation, Inc.

* cited by examiner

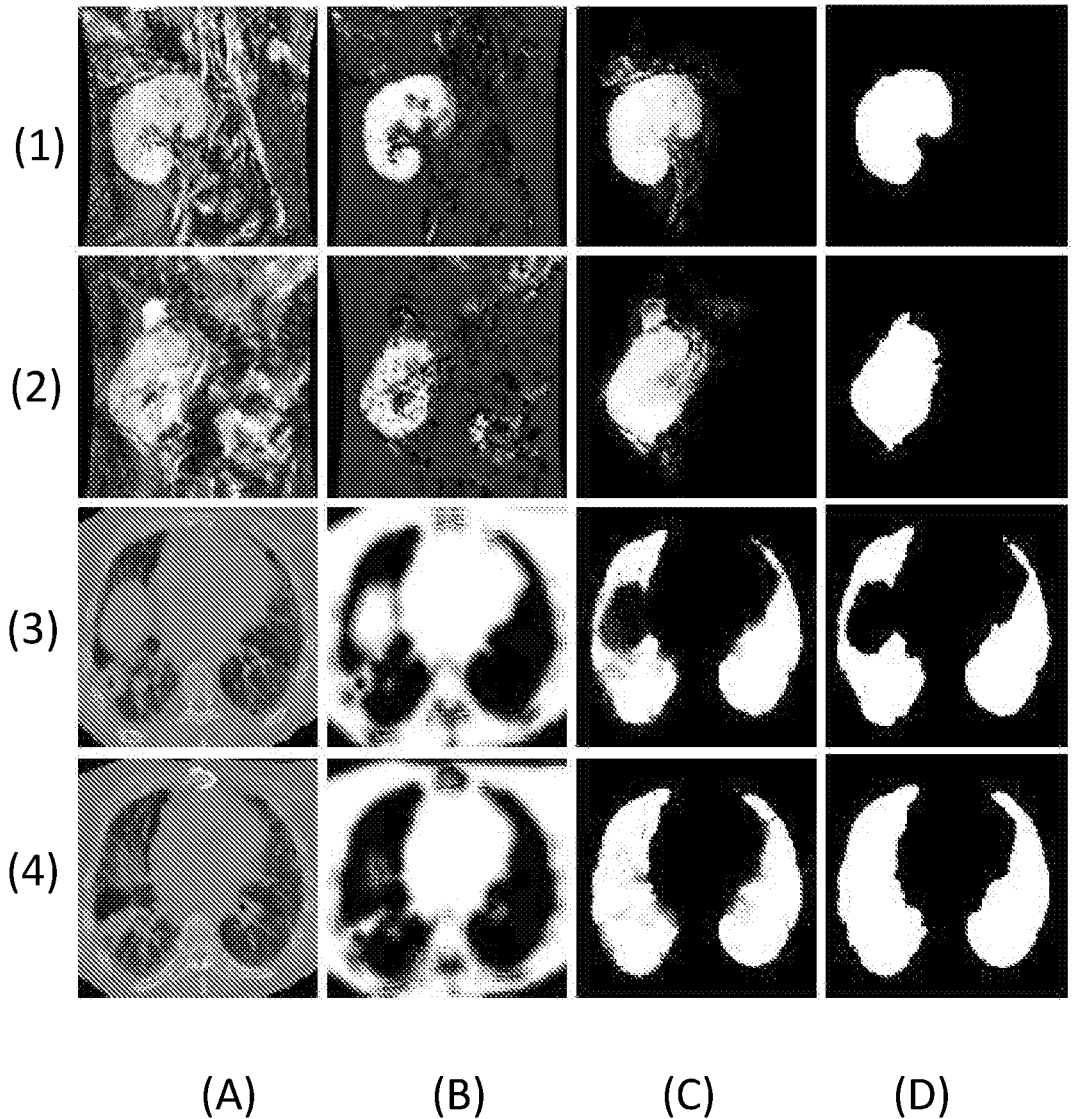
(A) (B) (C) (D)

SEGMENTATION OF MEDICAL IMAGES

This application claims the benefit of U.S. provisional patent application Ser. No. 62/529,788, filed Jul. 7, 2017, for PRECISE SEGMENTATION OF MEDICAL IMAGES BY GUIDING ADAPTIVE SHAPE WITH A 7TH-ORDER MGRF MODEL OF VISUAL APPEARANCE, incorporated herein by reference.

FIELD OF THE INVENTION

Methods for segmenting medical images from different modalities include integrating a plurality of types of quantitative image descriptors with a deep 3D convolutional neural network. The descriptors include: (i) a Gibbs energy for a prelearned 7th-order Markov-Gibbs random field (MGRF) model of visual appearance, (ii) an adaptive shape prior model, and (iii) a first-order appearance model of the original volume to be segmented. The neural network fuses the computed descriptors, together with the raw image data, for obtaining the final voxel-wise probabilities of the goal regions.

BACKGROUND OF THE INVENTION

Segmentation is a key first step in medical image processing and analysis. Accuracy in segmentation is necessary to generate accurate results in later steps of medical image processing and analysis, such as, for example, co-registration of different images, feature extraction, and computer aided detection or diagnostics (CAD). However, a robust and accurate segmentation is still a challenge due to various acquisition techniques for different imaging modalities and their technical limitations, signal noise and inhomogenities, artefacts, and blurred boundaries between anatomical structures, pathologies that accompany most of the investigated subjects, complex and overlapping object—background signal distributions in many scans, and other factors.

Existing segmentation techniques meet with several limitations. Shape distortions of pathological organs are mostly not taken into consideration. Objective functions of active shape models are typically non-convex, making the evolution too sensitive to accurate initialization due to fast convergence to the closest local energy minima. Some level-set algorithms assume piecewise constant or smooth goal segments to evolve an active contour, despite this assumption generally not being valid for medical image segmentation.

SUMMARY

To overcome these limitations and deal with various challenging normal and pathological organs, the disclosed method combines two shape and appearance descriptors of objects under consideration with a multi-channel deep 3D convolutional neural network (deep-3D-CNN). The object appearance is quantified by coupling its high-order prelearned probabilistic model with a simple first-order appearance model of the object outlined at each current position of the evolving shape.

Disclosed herein is a novel framework for segmenting medical images from different modalities by integrating higher-order appearance and adaptive shape descriptors, in addition to the input image current appearance with a deep-3D-CNN. The segmentation results for lung CT scans and DW-MRI kidney scans achieved a high accuracy evidenced by the reported DSC (Dice similarity coefficients), BHD (bidirectional Hausdorff distance), and PVD (percentage volume difference) values.

This summary is provided to introduce a selection of the concepts that are described in further detail in the detailed description and drawings contained herein. This summary is not intended to identify any primary or essential features of the claimed subject matter. Some or all of the described features may be present in the corresponding independent or dependent claims, but should not be construed to be a limitation unless expressly recited in a particular claim. Each embodiment described herein is not necessarily intended to address every object described herein, and each embodiment does not necessarily include each feature described. Other forms, embodiments, objects, advantages, benefits, features, and aspects of the present invention will become apparent to one of skill in the art from the detailed description and drawings contained herein. Moreover, the various apparatuses and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

A better understanding of the present invention will be had upon reference to the following description in conjunction with the accompanying drawings.

FIG. 1 depicts 2D axial projections for (A) the original image, (B) Gibbs energy, (C) adaptive shape probability, and (D) overlay of the final segmentation. The original images in rows (1) and (2) are DW-MRI kidney scans. The original images in rows (3) and (4) are lung CT scans.

DETAILED DESCRIPTION OF THE PREFERRED EMBODIMENTS

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

To obtain the final segmentation, the learned adaptive shape prior and high-order appearance descriptor are integrated with the model of current raw image signals by using the deep-3D-CNN. Basic components of the proposed framework are detailed below.

Adaptive Shape Prior

The probabilistic feature "adaptive shape prior" recited in Algorithm 1 describes the shape of a specific object, i.e., the target organ or tissue intended for segmentation in the medical image. Traditional shape priors account for a co-aligned training database of imaging scans from subject patients, but do not include pathologies or even large anatomical inconsistencies. The adaptive shape prior disclosed herein provides both the global and local adaptation to an object to be segmented. Global adaptation constitutes selecting training subjects, which are most similar to the test subject, to contribute to a customized database. The local adaptation constitutes including local patch similarity weights in addition to the customized voxel-wise similarity. Adding the local similarities amplifies the shape prior, especially for images like DW-MRI with irregular contrast. The appearance-guided adaptive shape prior depends on a set (database) of pre-selected, manually-segmented, and co-aligned subjects for each organ of interest. Using known non-rigid registration techniques, each database subject and its "gold-standard", or ground-truth segmentation map are co-aligned to the reference template (selected as an intermediate size and shape of all subjects). Each organ database, $D=\{d_i=(s_i, m_i): i=1, 2, \ldots, N\}$, contains 3D scans, having been chosen to represent typical inter-subject variations, and their true region maps. The subjects were selected from available data sets using the principal component analysis (PCA). A customized, globally similar database, $D_{cus}$, is extracted from D for each 3D test subject t to be segmented. In so doing, $D_{cus}$ is co-aligned to the domain of D and normalized cross correlations (NCC) between the body region in the aligned test subject t and in each database image, $s_{I:i}$ are calculated for selecting the top J similar subjects; $J>1$.

The shape prior is adapted in accord with visual appearances of the test subject t and the customized training images, $D_{cus}$, at both the voxel and patch/cube levels. Each voxel r of the test subject t is mapped to the database lattice by a deformation field aligning t to the database $D_{cus}$. For the voxel-level adaptation, an initial search cube $C_r$ of size $n_{x:i} \times n_{y:i} \times n_{z:i}$ is centered at the mapped location r. The search focuses on all the atlas voxels with signal deviations to within a predefined fixed range, $\lambda$, from the mapped input signal, $t_r$. If such voxels are absent in the atlas, the cube size, $n_{x:i} \times n_{y:i} \times n_{z:i}$, increases iteratively until the voxels within the range $\lambda$ are found. If the final cube size is reached, the search is repeated for the increased range $\lambda$ until such voxels are found. At the next, patch level of adaptation, a local similarity weight, $w_{C_r}, C_j$, for each atlas subject cube is obtained by calculating the NCC between the test subject patch, $C_{t:r}$, and each contributing patch, $C_{j:r}$. Then the voxel-wise shape probabilities, $P_{sh:r}(k)$; $k \in K$, are estimated based on the found voxels of similar appearance and their region labels, in addition to the local similarity between the patches for the test and contributing training subjects.

Let $\mathbb{R}_{j:r} = \{\varphi: \varphi \in R; \varphi \in C_r; |g_{j:\varphi} - t_r| \leq \lambda\}$ be a subset of similar voxels within the cube $C_{j:r}$ in the training image $g_j$. Then the unnormalized local similarity weight for the voxel r is $$w_{t,j:r} = \frac{\sum_{\varphi \in \mathbb{R}_{j:r}} (t_\varphi - \mu_{t:r})(g_{j:\varphi} - \mu_{j:r})}{\sqrt{\sum_{\varphi \in \mathbb{R}_{j:r}} (t_\varphi - \mu_{t:r})^2} \sqrt{\sum_{\varphi \in \mathbb{R}_{j:r}} (g_{j:\varphi} - \mu_{j:r})^2}}$$

and their normalizing factor is $$w_{tot} = \Sigma_{j=1}^J w_{j:r}$$

(here, $\mu$ ... are the related mean signals).

Let $\delta(z)$ denote the Kronecker's delta-function: $\delta(0)=1$ and 0 otherwise. Then, as shown in Equation 1 below, $$P_{sh:r}(k) = \frac{1}{w_{tot}} \sum_{j=1}^{J} \frac{w_j}{R_{j:r}} \sum_{\varphi \in \mathbb{R}_{j:r}} \delta(k - m_{j:\varphi}) \quad (1)$$

Exemplary steps for generating the adaptive shape prior are detailed in Algorithm 1 below:

---
Algorithm 1-Adaptive shape prior algorithm
---

Input: Test image t; co-aligned training database $D = \{d_i = (s_i, m_i) : i = 1, \ldots, N\}$.
Output: 4D shape prior $P_{sh} = (P_{sh:r} : r \in R)$
1 begin
// Align t to D, get the deformation field, $\varphi$, mapping each test voxel to the database domain
// Select top J images by normalized cross correlation (NCC) with the co-aligned test image
2    foreach image $s_i \in D$ do 3
$$NCC_{t,s_i} = \frac{\sum_{r \in R}(t_r - \mu_t)(s_{i:r} - \mu s_i)}{\sqrt{\sum_{r \in R}(t_r - \mu_t)^2} \sqrt{\sum_{r \in R}(s_{i:r} - \mu s_i)^2}}$$

4    end
// Form the atlas $D_{cus}$ from J closest, by the NCC, training images.

| Algorithm 1-Adaptive shape prior algorithm |
| --- |
| 5      foreach voxel $r \in R$ do<br>// Map the voxel r to the atlas $D_{cus}$ using $\varphi$.<br>6         while matches between the signal $t_r$ and the atlas signals are not found do<br>          // Initialize the matching tolerance: $\lambda \leftarrow \lambda_{init}$<br>          // Loop until $\lambda$ reaches a predefined threshold $\sigma$<br>7            while $\lambda < \sigma$ do<br>              // Find within each search cube $C_{j:r}$, j = 1 . . . J in the atlas image $s_j \in D_{cus}$ the matching subset $\mathbb{R}_{j:r} = \{\varphi : \varphi \in C_r; \lvert t_r - g_{j:\varphi}\rvert \leq \lambda\}$ and calculate the similarity between the test image, t, and training image, $s_j$, using the NCC to get the weight<br><br>$$w_{t,j;r} \frac{\sum_{\varphi \in R_{j:r}} (t_\varphi - \mu_{t:r})(g_{j:\varphi} - \mu_{j:r})}{\sqrt{\sum_{\varphi \in R_{j:r}} (t_\varphi - \mu_{t:r})^2} \sqrt{\sum_{\varphi \in R_{j:r}} (g_{j:\varphi} - \mu_{j:r})^2}}$$<br><br>8            if matching voxels are found in at least one $C_{j:r}$ then<br>              // Compute the voxel-wise region label probability $P_{sh:r}(k)$; $k \in \{0,1\}$, using the training labels and the numbers of voxels $R_{j:r}$ in the subsets $\mathbb{R}_{j:r}$ and the patch similarity weight $w_{t,j}$<br><br>9   $R_r \leftarrow \sum_{j=1}^{J} R_{j:r}; w_{tot} \leftarrow \sum_{j=1}^{J} w_{j:r}; P_{sh:r}(k) \leftarrow \frac{1}{R_r w_{tot}} \sum_{j=1}^{J} w_j \sum_{\varphi \in R_{j:r}} \delta(k - m_{j:\varphi}); k = 0, 1$<br><br>10            break<br>11            else<br>              // increment the matching threshold<br>12              $\lambda \leftarrow \lambda + \Delta_\lambda$<br>13            end<br>14          end<br>           // increment the search cube size<br>15          a $\leftarrow$ a + $\Delta_{size}$<br>16        end<br>17      end<br>18      return $P_{sh}$<br>19   end |

High-Order MGRF Model of Visual Appearance

To build this model, grayscale patterns of the goal objects, i.e., the organs, tissues, or other objects of interest in the medical image, are considered samples of a trainable translation- and contrast-offset-invariant 7th-order MGRF. The model relates the probability of an image texture, $g=(g(r):r\in \mathbb{R})$, with voxel-wise HU $g(r)$ to the Gibbs energy, $E_7$ (g), in a general-case exponential family distribution: $P_7(g)=(1/Z) \psi(g)\exp(-E_7(g))$. Here, Z is the normalizing factor.

To describe visual appearance of the target object with due account of how the training subjects have been affected, signal dependencies, called interactions, between each voxel and its seven neighbors are quantified in terms of simultaneous partial ordinal relations between the voxel-wise signals to within a fixed distance, $\rho$, from the voxel. To compute the energy $E_7$ (g), Gibbs potentials, $v_{7:\rho}(g(r'):r'\in \mathbb{R}(r))$, of translation-invariant 7-voxel subsets, are learned from a known training image, $g^o$, by using their approximate maximum likelihood estimates (MLE). These MLEs generalize the like analytical approximations of the potentials for a generic 2nd-order MGRF as:

$$v_{7:\rho}(\beta) = \frac{F_{7:\rho:core}(\beta) - F_{7:\rho}(\beta \mid g^o)}{F_{7:\rho:core}(\beta)(1 - F_{7:\rho:core}(\beta))}; \beta \in \mathbb{B}_7$$

Here, $\beta$ is a numerically coded contrast-offset-invariant relation between seven signals; $\mathbb{B}_7$ denotes the set of these codes for all possible ordinal 7-signal relations; $F_{7:\rho}$ ($g^o$) is an empirical marginal probability of the code $\beta$; $\beta \in \mathbb{B}_7$, over all the 7-voxel configurations with the center-to-voxel distance $\rho$ in $g^o$, and $F_{7:\rho:core}(\beta)$ is the like probability for the core distribution. The computed energy indicates the object presence: the lower the energy, the higher the object's probability.

The object and background appearances are quantified below by the voxel-wise Gibbs energies for the three similar 7th-order MGRFs, each with a single family of fixed-shape central-symmetric voxel configurations $\mathbb{R}(r=(x, y, z))=\{(x, y, z); (x\pm\rho, y, z), (x, y\pm\rho, z), (x, y, z\pm\rho)\}$. Their potentials and distances, $\rho$, between the peripheral and central voxels are learned from the training image, $g^o$.

Steps for learning the 7th-order MGRF appearance model are detailed in Algorithm 2 below:

Algorithm 2—Learning the 7th-Order MGRF Appearance Model

1. Given a training images $g^o$, find the empirical object (k=1) and background (k=0) probability distributions, $F_{l:7r}(g^o)=[F_{l:7r}(\beta|g^o):\beta\in \mathbb{B}]$ of the local binary pattern (LBP)-based descriptors for different clique sizes $r\in \{1, \ldots, r_{max}\}$ where the top size $r_{max}=10$.

2. Compute the empirical distributions $F_{7:r:core}=[F_{7:r:core}(\beta):\beta\in \mathbb{B}]$ of the same descriptors for the core IRF $\varphi(g)$, e.g., for an image, sampled from the core.

3. Compute the approximate MLE of the potentials:

$$V_{l:7:r}(\beta) = \frac{F_{7:r:core}(\beta) - F_{l:7:r}(\beta \mid g°)}{F_{7:r:core}(\beta) \cdot (1 - F_{7:r:core}(\beta))}$$

4. Compute partial Gibbs energies of the descriptors for equal and all other clique-wise signals over the training image for the clique sizes r=1,2, . . . ,10 to choose the size $p_l$, making both the energies the closest one to another.

Deep-3D-CNN Based Tissue Classification and Segmentation

For the final segmentation, the adaptive shape prior, the Gibbs energies with potentials from the learned 7th-order MGRF models, and the first-order appearance model of the original volume to be segmented, are used as inputs of a deep-3D-CNN. The CNN uses this data to generate probabilities that a given voxel in a raw data image is a goal region (e.g., the region of the medical image corresponding to a biological feature of interest, such as lungs in a chest CT scan, blood vessels in a retinal scan, etc.), then outputs a final segmented image. The first-order appearance model of the original volume to be segmented is simply the original, unmodified medical image. To output a final labeled region map of the segmented input image, the deep-3D-CNN generates soft-segmentation maps followed by a fully-connected classifier based on a 3D conditional random field (CRF). The input is sequentially convolved with multiple filters at the cascaded network layers, each consisting of a number of channels. Each channel corresponds to the 3D volume of a single calculated feature.

Considering the 3D input feature volumes at the first layer the input channels, the whole process can be viewed as convolving 4D volumes (the concatenated 3D feature volumes) with 4D kernels. The used CNN architecture consists of seven layers with the kernels of size $5^3$. The size of the receptive field (i.e., of the Input voxel neighborhood influencing the activation of a neuron) is $17^3$, while the classification layer has a single kernel. The advantage of this architecture is its ability to fuse and capture comprehensive 3D contextual information from the input feature volumes. The configuration parameters have been chosen heuristically. In other embodiments, fewer or greater numbers of layers may be used, and different kernel sizes and receptive field sizes may be used.

Experimentation

The proposed framework has been tested on two medical imaging modalities for different organs, namely, on chest CT scans to segment the lungs and abdominal DW-MRI to segment the kidneys. The chest scans have been locally collected from 95 subjects (control and diagnosed with different diseases). Data spacing for the data collected ranges from 1.17×1.17×2.0 mm to 1.37×1.37×3.0 mm. The DW-MRI volumes had been collected from 53 subjects at different b-values, in total, 583 DW-MRI data sets with b-values from 0 to 1000 s/mm² and the voxel of size 1.3281×1.3281×4.00 mm³, using a SIGNA Horizon scanner (General Electric Medical Systems, Milwaukee Wis.). The gold-standard segmentations for training and verification of tests were manually delineated by a medical imaging expert. To obtain different features for training our deep-3D-CNN network, it was applied in a leave-one-subject-out mode to segment objects inside the VOI determined by the body mask for each input scan. A minimal morphological post-processing to fill holes and remove scattered voxels was used for refinement. To accelerate convergence by reducing the internal covariant shift, the raw signals and modeled features for each input VOI were normalized to zero mean and unit standard deviation.

Testing performance has been evaluated in terms of the numbers of true positive (TP), true negative (TN), false positive (FP), and false negative (FN) voxels to measure the segmentation accuracy Acc=(TP+TN)/(TP+TN+FP+FN), sensitivity Sens=TP/(TP+FN), and specificity Spec=TN/(TN+FP). Table 1 lists these measures for different feature groups (FG), using only the appearance model of the raw signals (FG1), FG1 together with the learned seventh order Markov-Gibbs random field appearance model (FG2), and FG2 together with the adaptive shape prior (FG3). Clearly the combined features achieve the highest accuracy due to complementing each other in both normal and challenging pathological cases. The segmentation accuracy for each subject has been evaluated also using the DSC, BHD, and PVD metrics, which characterize the voxel-to-voxel similarities, the maximum surface-to-surface deviations, and the volume differences, respectively, between the region maps obtained and their ground truth. Table 1 summarizes the DSC, BHD, and PVD statistics for all the test subjects for the different FGs in the proposed framework. In particular, the mean ±standard deviation values of the DSC, BHD, and PVD for all the test subjects are 96.65±2.15%, 4.32±3.09 mm, and 5.61±3.37%, respectively for the segmented kidneys, and 98.37±0.68%, 2.79±1.32 mm, and 3.94±2.11%, respectively for the lungs. FIG. 1 exemplifies the segmentations and shows some generated features. In particular, column (A) in FIG. 1 depicts original, unmodified medical images and column (D) depicts final labeled images. As indicated in Table 1 below, combining the, which corresponds to the method disclosed herein, combining the seventh order Markov-Gibbs random field appearance model together with the adaptive shape prior provides the greatest accuracy, sensitivity, and specificity, and the most favorable DSC, BHD, and PVD, as compared to the MGRF alone or the raw image data.

TABLE 1

Deep-3D-CNN performance for the feature groups FG1, FG2, and FG3, evaluated by Acc, Sens, Spec, DSC (Dice similarity coefficient), BHD (bidirectional Hausdorff distance), and PVD (percentage volume difference).

| Tissue | Feature Group | Classification | | | Segmentation | | |
| --- | --- | --- | --- | --- | --- | --- | --- |
| | | Acc | Sens | Spec | DSC | BHD | PVD |
| Lung | FG1 | 93.21 ± 0.24 | 93.97 ± 0.62 | 94.81 ± 0.30 | 91.12 ± 2.62 | 9.95 ± 4.20 | 8.27 ± 3.15 |
| Lung | FG2 | 96.19 ± 0.49 | 96.17 ± 1.29 | 96.20 ± 0.74 | 95.99 ± 2.11 | 8.92 ± 3.42 | 5.23 ± 2.87 |
| Lung | FG3 | 99.01 ± 0.50 | 98.87 ± 0:32 | 99.11 ± 0:01 | 98.37 ± 0.68 | 2.79 ± 1.32 | 3.94 ± 2.11 |
| Kidney | FG1 | 90.51 ± 0.38 | 88.32 ± 2:90 | 99.34 ± 0.82 | 81.58 ± 12.69 | 20.34 ± 11.53 | 13.50 ± 12.72 |

TABLE 1-continued

Deep-3D-CNN performance for the feature groups FG1, FG2, and FG3, evaluated by Acc, Sens, Spec, DSC (Dice similarity coefficient), BHD (bidirectional Hausdorff distance), and PVD (percentage volume difference).

| Tissue | Feature Group | Classification | | | Segmentation | | |
|---|---|---|---|---|---|---|---|
| | | Acc | Sens | Spec | DSC | BHD | PVD |
| Kidney | FG2 | 92.75 ± 0.21 | 89.41 ± 3:88 | 99.83 ± 0.12 | 90.30 ± 7.74 | 11.49 ± 3.27 | 9.82 ± 8.57 |
| Kidney | FG3 | 98.21 ± 0.45 | 93.44 ± 2.40 | 99.91 ± 0.02 | 96.65 ± 2.15 | 4.32 ± 3.09 | 5.61 ± 3.37 |

Various aspects of different embodiments of the present invention are expressed in paragraphs X1 and X2 as follows:

X1. One aspect of the present invention pertains to a method for segmenting medical images comprising integrating image descriptors with a three dimensional neural network, the image descriptors including a medical image, a Gibbs energy for a Markov-Gibbs random field model of the medical image, and an adaptive shape prior model of the medical image; generating, using the three dimensional neural network, probabilities for a goal region; and designating, based on the generated probabilities, the goal region in the medical image.

X2. Another aspect of the present invention pertains to a method for segmenting medical images comprising receiving a medical image including a plurality of voxels; inputting into a neural network a plurality of image descriptors describing the medical image, wherein the plurality of image descriptors include a Gibbs energy for a Markov-Gibbs random field model, an adaptive shape prior model, and a first-order appearance model of the original volume to be segmented; calculating, by the neural network, probabilities that each voxel represents a goal region in the medical image; and segmenting, by the neural network, the medical image to identify the goal region.

X3. A further aspect of the present invention pertains to a method for segmenting a three-dimensional medical image, comprising receiving medical image data representing a three-dimensional medical image, the medical image data including a plurality of voxels; integrating a plurality of image descriptors of the medical image using a neural network; and outputting, by the neural network, segmentation data relating to the three-dimensional medical image, wherein the segmentation data is based on the plurality of integrated image descriptors.

et other embodiments pertain to any of the previous statements X1 or X2 which are combined with one or more of the following other aspects.

Wherein the goal region is a region of the medical image corresponding to a biological feature of interest.

Wherein the goal region is a region of the medical image corresponding to a kidney, a lung, a heart, one or more blood vessels, a liver, a bladder, a stomach, a brain, or an intestine.

Wherein the Gibbs energy for the Markov-Gibbs random field model is a Gibbs energy for a 7th-order Markov-Gibbs random field model.

Wherein the goal region is a region of the medical image corresponding to a biological feature of interest, and wherein the exemplary goal objects are the same biological feature.

Wherein the adaptive shape prior depends on a set of manually-segmented co-aligned subject images of a biological feature of interest corresponding to the goal region.

Wherein the medical image includes a plurality of voxels, and wherein the generating comprises generating probabilities that each voxel depicts a biological feature of interest.

Further comprising outputting a segmented medical image identifying the goal region.

Wherein the first-order appearance model of the original volume to be segmented is the medical image.

Further comprising outputting a segmented medical image identifying the goal region.

Wherein the Markov-Gibbs random field model is generated by using grayscale patterns of exemplary goal objects as samples of a trainable Markov-Gibbs random field.

Wherein the adaptive shape prior model is generated by adapting a shape prior in accord with the medical image and a database of customized training images.

Wherein the plurality of image descriptors include the medical image and a Gibbs energy for a Markov-Gibbs random field model of the medical image.

Wherein the plurality of image descriptors include the medical image and an adaptive shape prior model.

Wherein the segmentation data identifies a goal region in the medical image.

The foregoing detailed description is given primarily for clearness of understanding and no unnecessary limitations are to be understood therefrom, for modifications can be made by those skilled in the art upon reading this disclosure and may be made without departing from the spirit of the invention. Although specific spatial dimensions are stated herein, such specific quantities are presented as examples only.

What is claimed is:

1. A method for segmenting medical images comprising:
   integrating image descriptors with a three-dimensional neural network, the image descriptors including a medical image, a Gibbs energy for a Markov-Gibbs random field model of the medical image, and an adaptive shape prior model of the medical image;
   generating, using the three-dimensional neural network, probabilities for a goal region; and
   designating, based on the generated probabilities, the goal region in the medical image.

2. The method of claim 1, wherein the goal region is a region of the medical image corresponding to a biological feature of interest.

3. The method of claim 1, wherein the Gibbs energy for the Markov-Gibbs random field model is a Gibbs energy for a 7th-order Markov-Gibbs random field model.

4. The method of claim 1, wherein the Markov-Gibbs random field model is generated by using grayscale patterns of exemplary goal objects as samples of a trainable Markov-Gibbs random field.

5. The method of claim 4, wherein the goal region is a region of the medical image corresponding to a biological feature of interest, and wherein the exemplary goal objects are the same biological feature.

6. The method of claim 1, wherein the adaptive shape prior depends on a set of manually-segmented co-aligned subject images of a biological feature of interest corresponding to the goal region.

7. The method of claim 1, wherein the medical image includes a plurality of voxels, and wherein the generating comprises generating probabilities that each voxel depicts a biological feature of interest.

8. The method of claim 1, further comprising outputting a segmented medical image identifying the goal region.

9. A method for segmenting medical images comprising:
   receiving a medical image including a plurality of voxels;
   inputting into a three-dimensional neural network a plurality of image descriptors describing the medical image, wherein the plurality of image descriptors include a Gibbs energy for a Markov-Gibbs random field model, an adaptive shape prior model, and a first-order appearance model of the original volume to be segmented;
   calculating, by the neural network, probabilities that each voxel represents a goal region in the medical image; and
   segmenting, by the neural network, the medical image to identify the goal region.

10. The method of claim 9, wherein the goal region is a region of the medical image corresponding to a biological feature of interest.

11. The method of claim 9, wherein the first-order appearance model of the original volume to be segmented is the medical image.

12. The method of claim 9, further comprising outputting a segmented medical image identifying the goal region.

13. The method of claim 9, wherein the Markov-Gibbs random field model is generated by using grayscale patterns of exemplary goal objects as samples of a trainable Markov-Gibbs random field.

14. The method of claim 9, wherein the adaptive shape prior model is generated by adapting a shape prior in accord with the medical image and a database of customized training images.

15. A method for segmenting a three-dimensional medical image, comprising:
   receiving medical image data representing a three-dimensional medical image, the medical image data including a plurality of voxels;
   integrating a plurality of image descriptors of the medical image using a three-dimensional neural network; and
   outputting, by the neural network, segmentation data relating to the three-dimensional medical image, wherein the segmentation data is based on the plurality of integrated image descriptors;
   wherein the plurality of image descriptors include the medical image and a Gibbs energy for a Markov-Gibbs random field model of the medical image.

16. The method of claim 15, wherein the plurality of image descriptors further include an adaptive shape prior model.

17. The method of claim 15, wherein the segmentation data identifies a goal region in the medical image.

* * * * *